(12) United States Patent
Hsueh

(10) Patent No.: US 11,197,705 B2
(45) Date of Patent: Dec. 14, 2021

(54) BONE CEMENT INJECTION DEVICE

(71) Applicant: Shao-Kang Hsueh, Taipei (TW)

(72) Inventor: Shao-Kang Hsueh, Taipei (TW)

( * ) Notice: Subject to any disclaimer, the term of this patent is extended or adjusted under 35 U.S.C. 154(b) by 323 days.

(21) Appl. No.: 16/520,360

(22) Filed: Jul. 24, 2019

(65) Prior Publication Data

US 2021/0022785 A1 Jan. 28, 2021

(51) Int. Cl.
*A61B 17/88* (2006.01)
*A61B 17/56* (2006.01)

(52) U.S. Cl.
CPC ...... *A61B 17/8816* (2013.01); *A61B 17/8811* (2013.01); *A61B 17/8822* (2013.01); *A61B 2017/564* (2013.01)

(58) Field of Classification Search
CPC ............................... A61B 17/8802–2017/8838
See application file for complete search history.

(56) References Cited

U.S. PATENT DOCUMENTS

| 5,265,956 | A | * | 11/1993 | Nelson | A61B 17/8822 |
| | | | | | 141/23 |
| 2007/0055261 | A1 | * | 3/2007 | Reiley | A61B 17/22012 |
| | | | | | 606/79 |
| 2007/0093759 | A1 | * | 4/2007 | Sickler | A61M 5/31511 |
| | | | | | 604/181 |
| 2012/0026823 | A1 | * | 2/2012 | Greter | B01F 11/0082 |
| | | | | | 366/130 |
| 2012/0092951 | A1 | * | 4/2012 | Faccioli | B01F 13/0023 |
| | | | | | 366/267 |
| 2017/0258507 | A1 | * | 9/2017 | Hetherington | A61M 5/31511 |
| 2017/0296247 | A1 | * | 10/2017 | Hsueh | A61B 17/8825 |

* cited by examiner

*Primary Examiner* — Zade Coley
(74) *Attorney, Agent, or Firm* — Leong C. Lei

(57) ABSTRACT

The bone cement injection device includes an injection assembly and a filler assembly. The injection assembly includes a barrel, first needle member, second needle member, and plunger. The first needle member is movably housed inside the barrel, and includes a first member body, a first conduit, a side tube, and puller elements. The second needle member is housed in the first needle member, and includes a second member body, and a second conduit. A space is maintained between the first and second conduits. The plunger is joined to the first member body and is movably housed in the second member body. The filler assembly fills bone cement into the second member body. The first needle member is pulled backward, and the plunger injects the bone cement into the patient's bone. With an air compressor connected to the side tube, a negative pressure is created to facilitate bone cement injection.

10 Claims, 7 Drawing Sheets

BONE CEMENT INJECTION DEVICE

BACKGROUND OF THE INVENTION

(a) Technical Field of the Invention

The present invention is generally related to bone cement injection devices, and more particular to a convenient, effort-saving, and fast bone cement injection device.

(b) Description of the Prior Art

Bone cement is a medical material often applied in various bone-related operations such as artificial knee joint, hip joint replacement, and vertebroplasty, etc. Specifically, vertebroplasty is commonly used for Spinal compression fracture or deformation resulted from osteoporosis, or for skeletal destruction and pain caused by metastatictumorofbone. For these operations, an injection device is required to inject bone cement into a patient's bone. Taiwan Utility Model Patent Nos. M421803, M430285, and M346407 all teach various bone cement injection devices. These teachings have complex structures, and they often rely on a screw that, by twisting the screw, pushes the bone cement into the patient's bone. However, there are blood, air, and water inside the bone's enclosed space, doctors have to exercise a significant amount of effort in injecting the bone cement. The injection process is, therefore, inconvenient and slow. The doctors as such suffer great pressure and psychological burden. If the operation is not carefully conducted, the patient may get infection or even develops pulmonary embolism.

SUMMARY OF THE INVENTION

Major objectives of the present invention is to have a filler assembly filling bone cement in an injection assembly, to provide a first needle member facilitating a plunger to inject bone cement from a second needle member into a patient's bone, to assist the injection by creating a negative pressure through connecting an air compressor to a side tube to draw blood, water, and air out of the bone so that bone cement may be conveniently introduced into the bone with less effort and fast speed.

To achieve the objectives, the bone cement injection device comprises an injection assembly. The injection assembly comprises a barrel, a first needle member, a second needle member, and a plunger; the barrel has two opposing slots configured axially along the barrel's circumference; the first needle member is movably housed inside the barrel; the first needle member comprises a first member body, a first conduit extended axially from a first end of the first member body, a side tube extended radially from a side of the first member body, and two puller elements respectively disposed to two sides of a second end of the first member body; the side tube and the puller elements are respectively received by the slots; the second needle member is housed in the first needle member; the second needle member comprises a second member body, and a second conduit extended from a first end of the second member body; the second member body is enclosed in the first member body; the second conduit is threaded through the first conduit; a space is maintained between the first conduit and the second conduit; and the plunger is joined to the first member body and is movably housed in the second member body.

In one embodiment, the bone cement injection device further comprises a filler assembly for filling bone cement in the injection assembly. The filler assembly comprises a filler barrel, a filler plunger movably housed in the filler barrel, a funnel detachably mounted on a first end of the filler barrel, and a stirrer removably threaded into the filler barrel through the first end of the filler barrel.

In one embodiment, the filler barrel's first end has a first fastening element; and the funnel and the stirrer respectively have corresponding second fastening elements for detachably engaging the first fastening element.

In one embodiment, the filler barrel's first end has a first fastening element; and a second end of the second member body has a corresponding second fastening element for detachably engaging the first fastening element.

In one embodiment, the bone cement injection device further comprises a dial element rotatably configured around the barrel, and the dial element comprises a ring casing and at least two blocks housed in the ring casing.

In one embodiment, each block comprises a body movably configured inside the ring casing, two limiting blocks configured on an outer side of the body, two pins respectively embedded in the two limiting blocks, two elastic elements respectively disposed between the ring casing and the pins, a button extended from the outer side of the body and exposed outside the ring casing, and at least two ducts along an inner side of the body.

In one embodiment, there are two limiting ducts inside the ring casing; each limiting block has a protrusion on a top side removably fit in a limiting duct.

In one embodiment, there are two rows of teeth respectively along two opposing sides of the first member body; and each duct movably receives at least a tooth.

In one embodiment, outer threads are configured around the outer surface of a second end of the second member body; inner threads are configured around the inner surface of a second end of the first member body; and, by fastening the outer threads of the second member body with the inner threads of the first member body, the second member body and the first member body are reliably joined together.

In one embodiment, the plunger comprises a filler plunger movably housed in the second member body and a pusher element joined to the first member body and the filler plunger.

The foregoing objectives and summary provide only a brief introduction to the present invention. To fully appreciate these and other objects of the present invention as well as the invention itself, all of which will become apparent to those skilled in the art, the following detailed description of the invention and the claims should be read in conjunction with the accompanying drawings. Throughout the specification and drawings identical reference numerals refer to identical or similar parts.

Many other advantages and features of the present invention will become manifest to those versed in the art upon making reference to the detailed description and the accompanying sheets of drawings in which a preferred structural embodiment incorporating the principles of the present invention is shown by way of illustrative example.

DETAILED DESCRIPTION OF THE PREFERRED EMBODIMENTS

Figure 1:
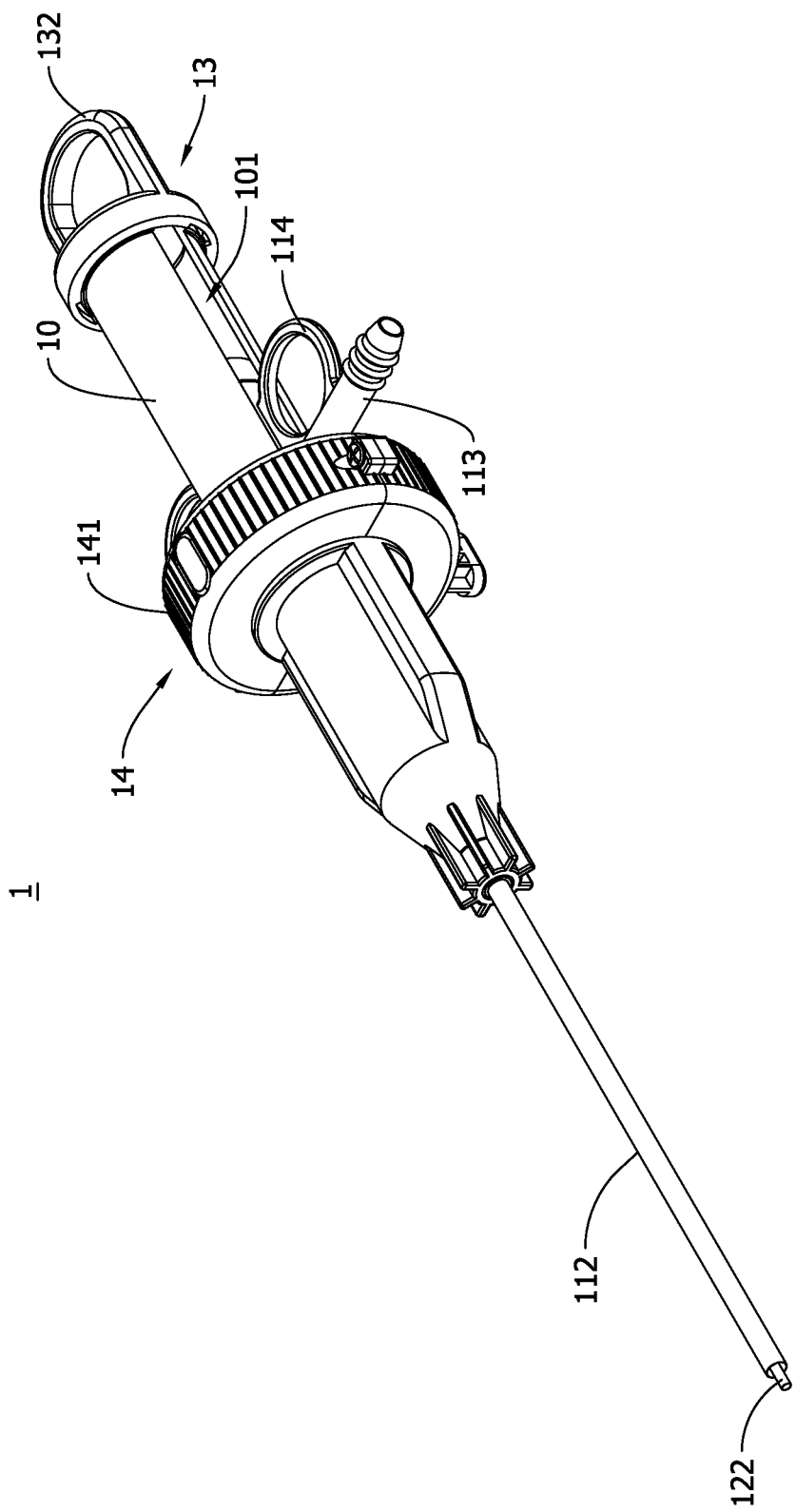
FIG. 1 is a perspective diagram showing an injection assembly of a bone cement injection device according to an embodiment of the present invention.

The following descriptions are exemplary embodiments only, and are not intended to limit the scope, applicability or configuration of the invention in any way. Rather, the following description provides a convenient illustration for implementing exemplary embodiments of the invention. Various changes to the described embodiments may be made in the function and arrangement of the elements described without departing from the scope of the invention as set forth in the appended claims.

As shown in FIGS. 1 to 7, a bone cement injection device according to an embodiment of the present invention includes an injection assembly 1 and a filler assembly 2. The filler assembly 2 fills the injection assembly 1 with bone cement. The injection assembly 1 includes a barrel 10, a first needle member 11, a second needle member 12, and a plunger 13.

The barrel 10 has two opposing slots 101 configured axially along the barrel 10's circumference.

The first needle member 11 is movably housed inside the barrel 10. The first needle member 11 includes a first member body 111, a first conduit 112 extended axially from a first end of the first member body 111, a side tube 113 extended radially from a side of the first member body 111, and two puller elements 114 respectively disposed to two sides of a second end of the first member body 111. The side tube 113 and the puller elements 114 are respectively received by the slots 101.

The second needle member 12 is housed in the first needle member 11. The second needle member 12 includes a second member body 121, a second conduit 122 extended from a first end of the second member body 121. The second member body 121 is enclosed in the first member body 111. The second conduit 122 is threaded through the first conduit 112. A space 123 is maintained between the first conduit 112 and the second conduit 122.

The plunger 13 is joined to the first member body 111 and is movably housed in the second member body 121.

Figure 3:
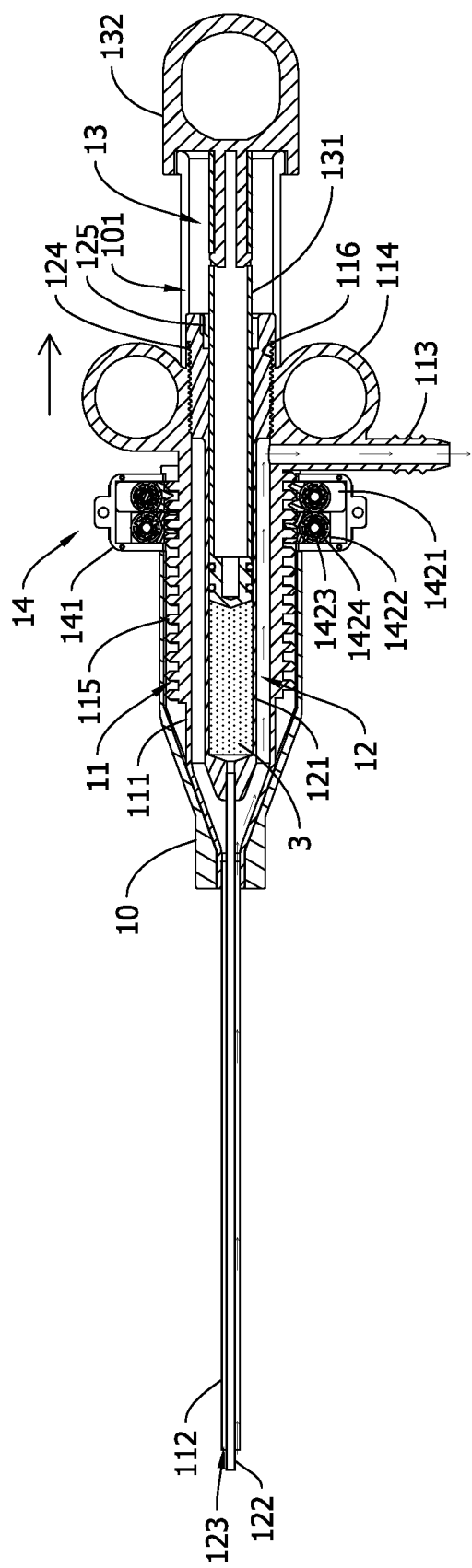
FIGS. 3 and 4 are sectional diagrams showing the injection assembly of FIG. 1 under usage.
Figure 4:
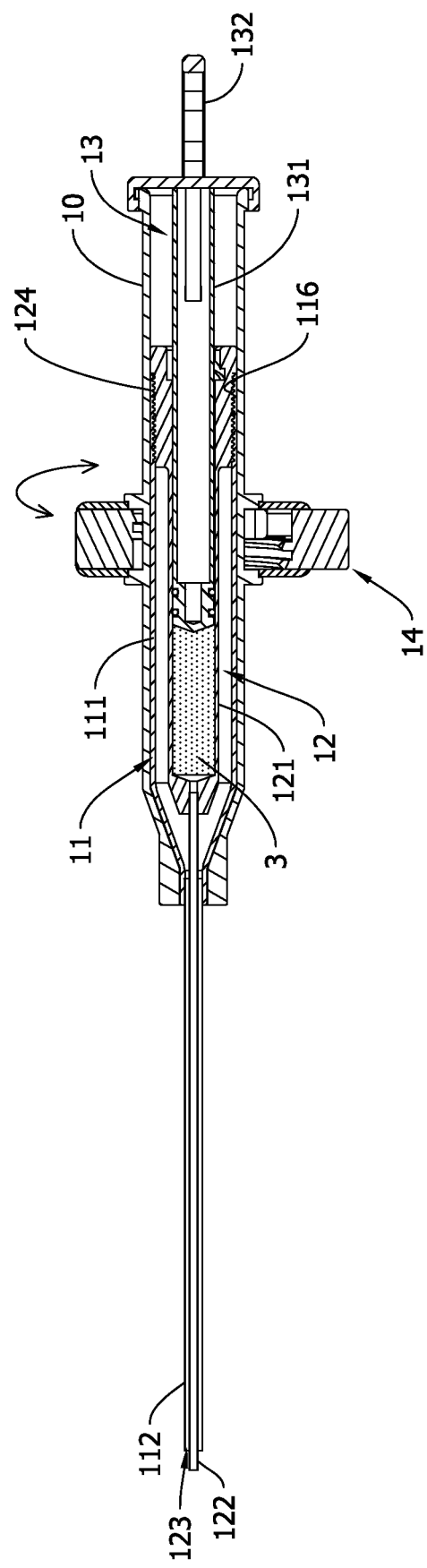
Figure 7:
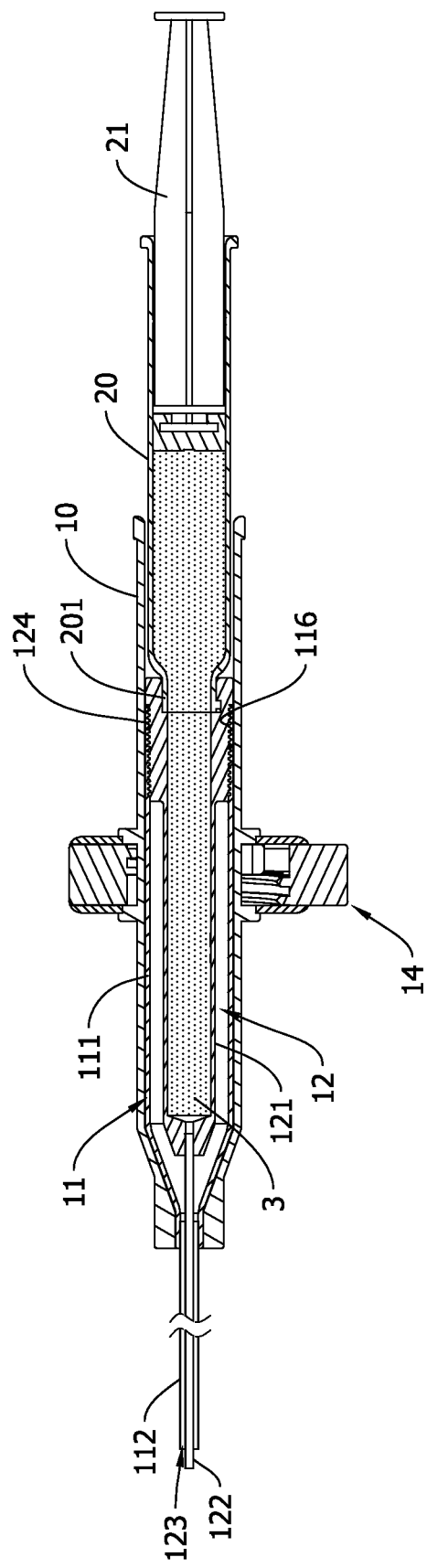
FIG. 7 is a sectional diagram showing the injection assembly of FIG. 1 joined with the filler assembly of FIG. 5.

As shown in FIG. 7, to operate the bone cement injection device, the filler assembly 2 fills bone cement 3 into the second member body 121 of the injection assembly 1 and the side tube 113 is connected to an air compressor (not shown). Then, the first conduit 112 and the second conduit 122 penetrates into a patient's bone and the air compressor is turned on. Through the puller elements 114, the slots 101 and the plunger 13, the first needle member 11 and the second needle member 12 are pulled backward within the barrel 10 so that the plunger 13 injects the bone cement 3 inside the second member body 121 into the patient's bone through the second conduit 122. In the meantime, with the assistance from the air compressor, the air, fat, blood, and water inside the bone is sucked out through the space 123 between the first conduit 112 and the second conduit 122, as shown in FIGS. 3 and 4. As the air, fat, blood, and water are sucked out, a negative pressure is induced, and the introduction of bone cement 3 into the bone is facilitated, thereby achieving convenient, effort-saving, and fast bone cement injection.

Figure 5:
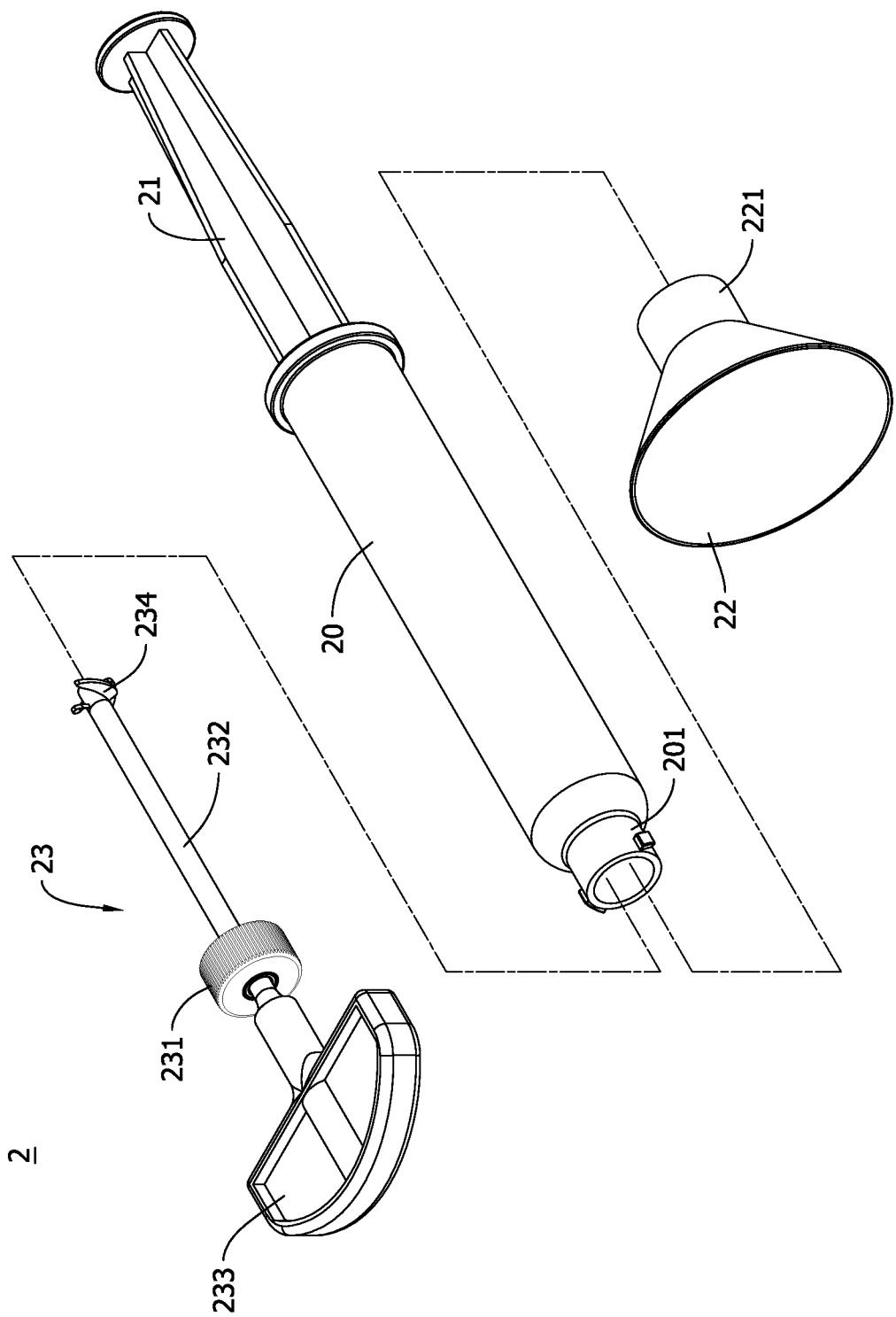
FIG. 5 is a perspective diagram showing a filler assembly of a bone cement injection device according to an embodiment of the present invention.
Figure 6:
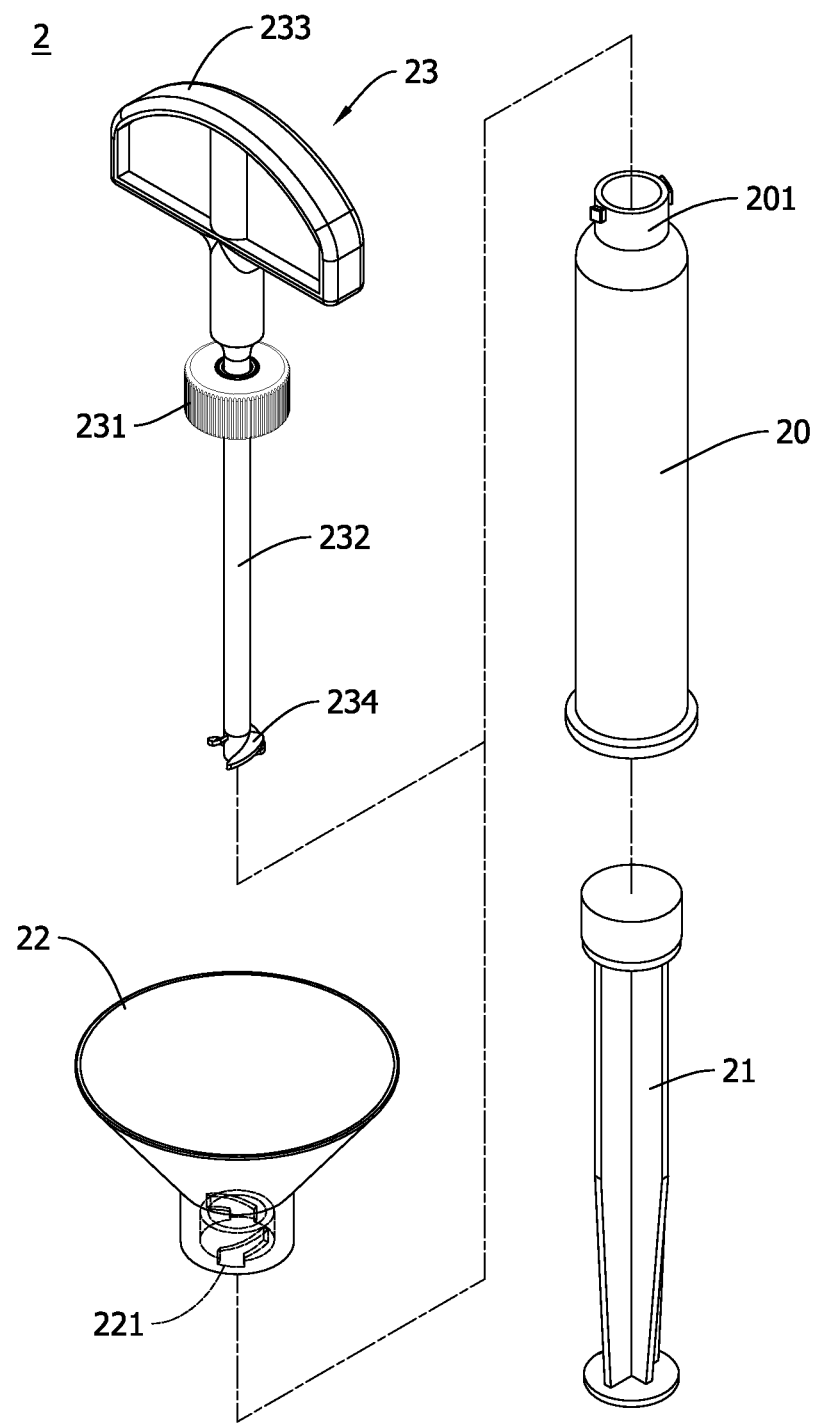
FIG. 6 is a perspective breakdown diagram showing the filler assembly of FIG. 5.

In the present embodiment, the filler assembly 2 includes a filler barrel 20, a filler plunger 21 movably housed in the filler barrel 20, a funnel 22 detachably mounted on a first end of the filler barrel 20, and a stirrer 23 that may be removably threaded into the filler barrel 20 through the first end of the filler barrel 20. The filler barrel 20's first end has a fastening element 201. As shown in FIGS. 5 and 6, the funnel 22 and the stirrer 23 respectively have corresponding fastening elements 221, 231 for detachably engaging the fastening element 201.

To prepare the bone cement 3, the filler plunger 21 is first pulled out of a second end of the filler barrel 20 but is not removed. The funnel 22 is joined to the first end of the filler barrel 20 by locking the fastening elements 221 and 201. The material for the bone cement 3 is poured into the filler barrel 20 through the funnel 22. Then the funnel 22 is removed by disengaging the fastening elements 221 and 201. Subsequently, the stirrer 23 is threaded into the filler barrel 20 and the fastening elements 231 and 201 are engaged so that a stirrer rod 232 of the stirrer 23 is inside the filler barrel 20. A swiveling element 233 at a first end of the stirrer 23 is twisted so that blades 234 at a second end of the stirrer 23 blends the material for bone cement 3 inside the filler barrel 20.

After the bone cement 3 is prepared as described above, the stirrer 23 is removed after disengaging the fastening elements 231 and 201. As shown in FIG. 7, the filler assembly 2 is joined to a second end of the second member body 121 by engaging the fastening element 201 and a fastening element 125 at the second end of the second member body 121. The filler plunger 21 then forces the bone cement 3 inside the filler barrel 20 into second member body 121 of the injection assembly 1 for subsequent injection operation by the injection assembly 1.

Figure 2:
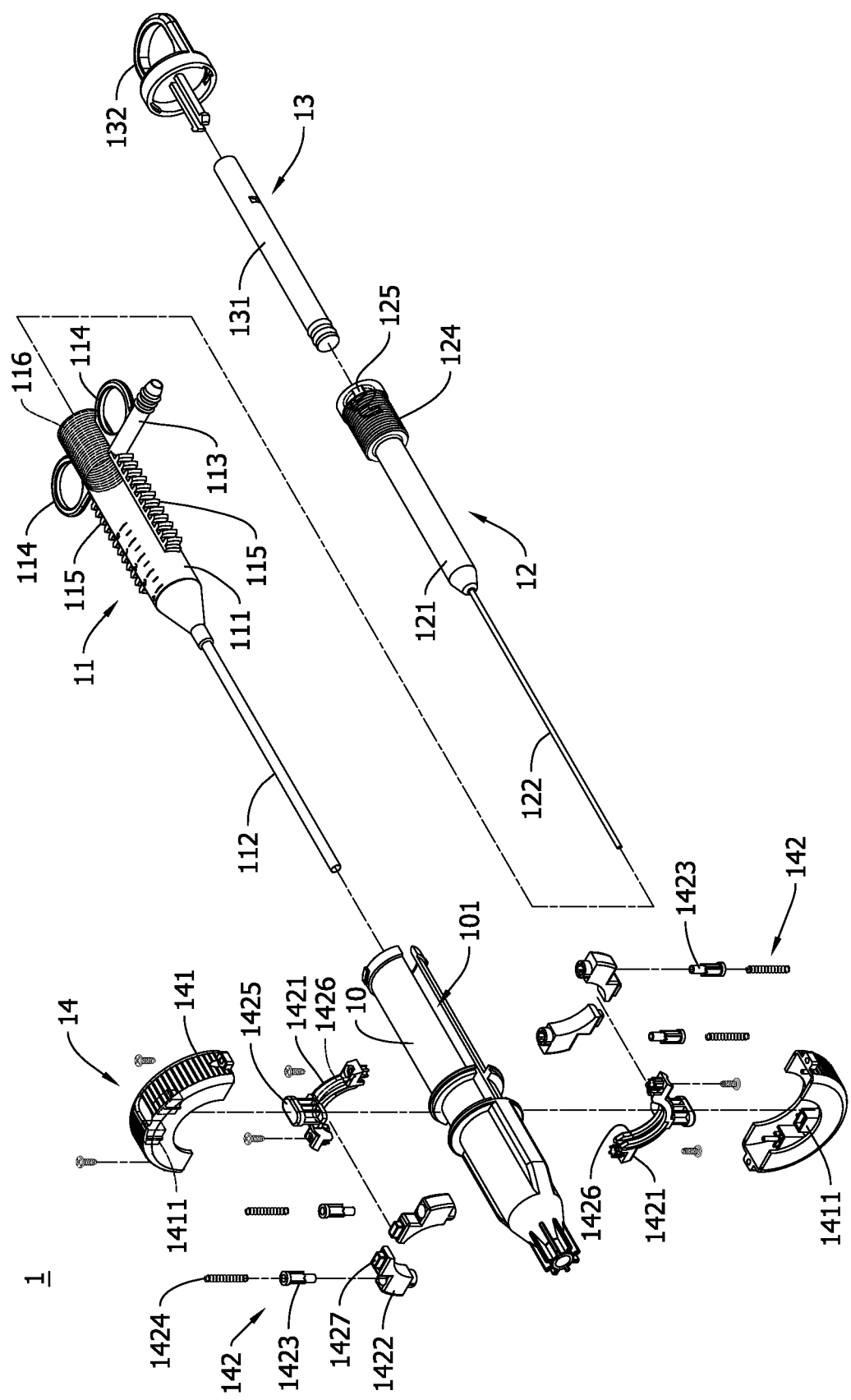
FIG. 2 is a perspective breakdown diagram showing the injection assembly of FIG. 1.

The present embodiment further includes a dial element 14. The dial element 14 rotatably configured around the barrel 10. The dial element 14 includes a ring casing 141, and at least two C-shaped blocks 142 housed in the ring casing 141. Each block 142 includes a body 1421 movably configured inside the ring casing 141, two limiting blocks 1422 configured on an outer side of the body 1421, two pins 1423 respectively embedded in the two limiting blocks 1422, and two elastic elements 1424 respectively disposed between the ring casing 141 and the pins 1423. A button 1425 is extended from the outer side of the body 1421 and exposed outside the ring casing 141. The body 1421's inner side has at least two ducts 1426. Inside the ring casing 141, there are two limiting ducts 1411. Each limiting block 1422 has a protrusion 1427 removably fit in a limiting duct 1411. Along two opposing sides of the first member body 111, there are respectively two rows of teeth 115. As shown in FIG. 2, each duct 1426 receives at least a tooth 115.

Therefore, when not using the puller elements 114 to inject the bone cement 3, the buttons 1425 may be depressed so that the bodies 1421 move towards the barrel 10. Through the pins 1423 and the elastic elements 1424, the bodies 1421 are positioned so that each duct 1426 receives at least a tooth 115. Then, turning the ring casing 141 would rotate the bodies 1421 as well, and the teeth 115 would sequentially move in and out the ducts 1426, thereby pulling the first needle member 11 and the second needle member 12 backward from within the barrel 10 so that the plunger 13 forces the bone cement 3 inside the second member body 121 into the patient's bone through the second conduit 122. In the meantime, the air compressor may be applied to draw the air, fat, blood, and water from the bone through the space 123 between the first conduit 112 and the second conduit 122. As such, as shown in FIGS. 1 to 4, depending on the operation requirement, the bone cement injection device of the present invention may be applied in various manners to inject the bone cement 3 with less effort and fast speed.

If the dial element 14 is not used, the buttons 1425 may be depressed again so that, through the push by the pins 1423 and the elastic elements 1424, the bodies 1421 move away from the barrel 10, the protrusions 1427 on the limiting blocks 1422 extend into the limiting ducts 1411, and the ducts 1426 disengage teeth 115. The bodies 1421 are as such restored to their original, undepressed position and ready for the next operation.

In the present embodiment, outer threads 124 are configured around the outer surface of a second end of the second member body 121, and inner threads 116 are configured around the inner surface of a second end of the first member body 111. By fastening the outer threads 124 of the second member body 121 with the inner threads 116 of the first member body 111, the second member body 121 and the first member body 111 are reliably joined, and they are not easily detached during operation, as shown in FIGS. 2 to 4.

In the present embodiment, the plunger 13 includes a filler plunger 131 movably housed in the second member body 121, and a pusher element 132 joined to the first member body 111 and the filler plunger 131, as shown in FIGS. 1 to 4. As such, when pulling the first needle member 11 and the second needle member 12 backward in the barrel 10 by the puller elements 114, the pusher element 132 may be pushed simultaneously so that the filler plunger 131 may inject the bone cement 3 inside the second member body 121 into the patient's bone through the second conduit 122.

As described above, the filler assembly fills bone cement into the second member body of the injection assembly. The first needle member is pulled backward through the puller elements, and the plunger injects the bone cement inside the second member body into the patient's bone. In the meantime, with the assistance from an air compressor connected to the side tube, the air, fat, blood, and water inside the bone is sucked out. As the air, fat, blood, and water are sucked out, a negative pressure is induced, and the introduction of bone cement into the bone is facilitated, thereby achieving convenient, effort-saving, and fast bone cement injection.

While certain novel features of this invention have been shown and described and are pointed out in the annexed claim, it is not intended to be limited to the details above, since it will be understood that various omissions, modifications, substitutions and changes in the forms and details of the device illustrated and in its operation can be made by those skilled in the art without departing in any way from the claims of the present invention.

I claim:

1. A bone cement injection device, comprising an injection assembly,
   wherein the injection assembly comprises a barrel, a first needle member, a second needle member, and a plunger;
   the barrel has two opposing slots configured axially along the barrel's circumference;
   the first needle member is movably housed inside the barrel; the first needle member comprises a first member body, a first conduit extended axially from a first end of the first member body, a side tube extended radially from a side of the first member body, and two puller elements respectively disposed to two sides of a second end of the first member body; the side tube and the puller elements are respectively received by the slots;
   the second needle member is housed in the first needle member; the second needle member comprises a second member body, and a second conduit extended from a first end of the second member body; the second member body is enclosed in the first member body; the second conduit is threaded through the first conduit; a space is maintained between the first conduit and the second conduit; and
   the plunger is joined to the first member body and is movably housed in the second member body.

2. The bone cement injection device according to claim 1, further comprising a filler assembly for filling bone cement in the injection assembly, wherein the filler assembly comprises a filler barrel, a filler plunger movably housed in the filler barrel, a funnel detachably mounted on a first end of the filler barrel, and a stirrer removably threaded into the filler barrel through the first end of the filler barrel.

3. The bone cement injection device according to claim 2, wherein the filler barrel's first end has a first fastening element; and the funnel and the stirrer respectively have corresponding second fastening elements for detachably engaging the first fastening element.

4. The bone cement injection device according to claim 2, wherein the filler barrel's first end has a first fastening element; and a second end of the second member body has a corresponding second fastening element for detachably engaging the first fastening element.

5. The bone cement injection device according to claim 1, further comprising a dial element rotatably configured around the barrel, wherein the dial element comprises a ring casing and at least two blocks housed in the ring casing.

6. The bone cement injection device according to claim 5, wherein each block comprises a body movably configured inside the ring casing, two limiting blocks configured on an outer side of the body, two pins respectively embedded in the two limiting blocks, two elastic elements respectively disposed between the ring casing and the pins, a button extended from the outer side of the body and exposed outside the ring casing, and at least two ducts along an inner side of the body.

7. The bone cement injection device according to claim 6, wherein there are two limiting ducts inside the ring casing; each limiting block has a protrusion on a top side removably fit in a limiting duct.

8. The bone cement injection device according to claim 6, wherein there are two rows of teeth respectively along two opposing sides of the first member body; and each duct movably receives at least a tooth.

9. The bone cement injection device according to claim 1, wherein outer threads are configured around the outer surface of a second end of the second member body; inner threads are configured around the inner surface of a second end of the first member body; and, by fastening the outer threads of the second member body with the inner threads of the first member body, the second member body and the first member body are reliably joined together.

10. The bone cement injection device according to claim 1, wherein the plunger comprises a filler plunger movably housed in the second member body and a pusher element joined to the first member body and the filler plunger.

* * * * *